United States Patent [19]

Saliga

[11] 4,338,951
[45] Jul. 13, 1982

[54] MAGNETICALLY COUPLED ISOLATION INTERFACE CIRCUIT

[75] Inventor: Thomas V. Saliga, Tampa, Fla.

[73] Assignee: Critikon, Inc., Tampa, Fla.

[21] Appl. No.: 179,614

[22] Filed: Aug. 19, 1980

[51] Int. Cl.³ .............................................. A61B 5/00
[52] U.S. Cl. .................................... 128/695; 128/908; 307/149
[58] Field of Search ................. 307/149, 326, 89, 91; 322/69; 361/35, 38, 57, 58, 59, 71, 74, 75, 87, 89, 96, 98, 100, 101; 336/70, 73, 84 M, 155, 174, 175, 229; 340/532

[56] References Cited

U.S. PATENT DOCUMENTS

| | | | |
|---|---|---|---|
| 3,431,487 | 3/1969 | Savage | 336/73 |
| 3,690,313 | 9/1972 | Weppner | 128/908 |
| 3,699,390 | 10/1972 | Blakeslee | 361/57 |
| 4,106,494 | 8/1978 | McEachern | 128/696 |
| 4,172,244 | 10/1979 | Zeis | 336/174 |
| 4,236,086 | 11/1980 | Hoebel | 307/326 |

Primary Examiner—William E. Kamm
Attorney, Agent, or Firm—Audley A. Ciamporcero, Jr.

[57] ABSTRACT

A pair of toroidally wound cores are maintained in a generally parallel, vertical, spaced apart relationship by a tubular insulating member passing through the toroid centers. The tubular member insulates the windings from a coupling loop which passes through the tube and which closes outside the toroidal windings. One winding is the primary of the isolation circuit, connecting the source of signals through a FET device to ground, and the other winding is secondary winding, which is also connected to ground through a FET, and which is coupled to a utilization device through a low pass filter. The FET devices are synchronously pulsed at a frequency above the signal frequency and the filter pass band.

6 Claims, 5 Drawing Figures

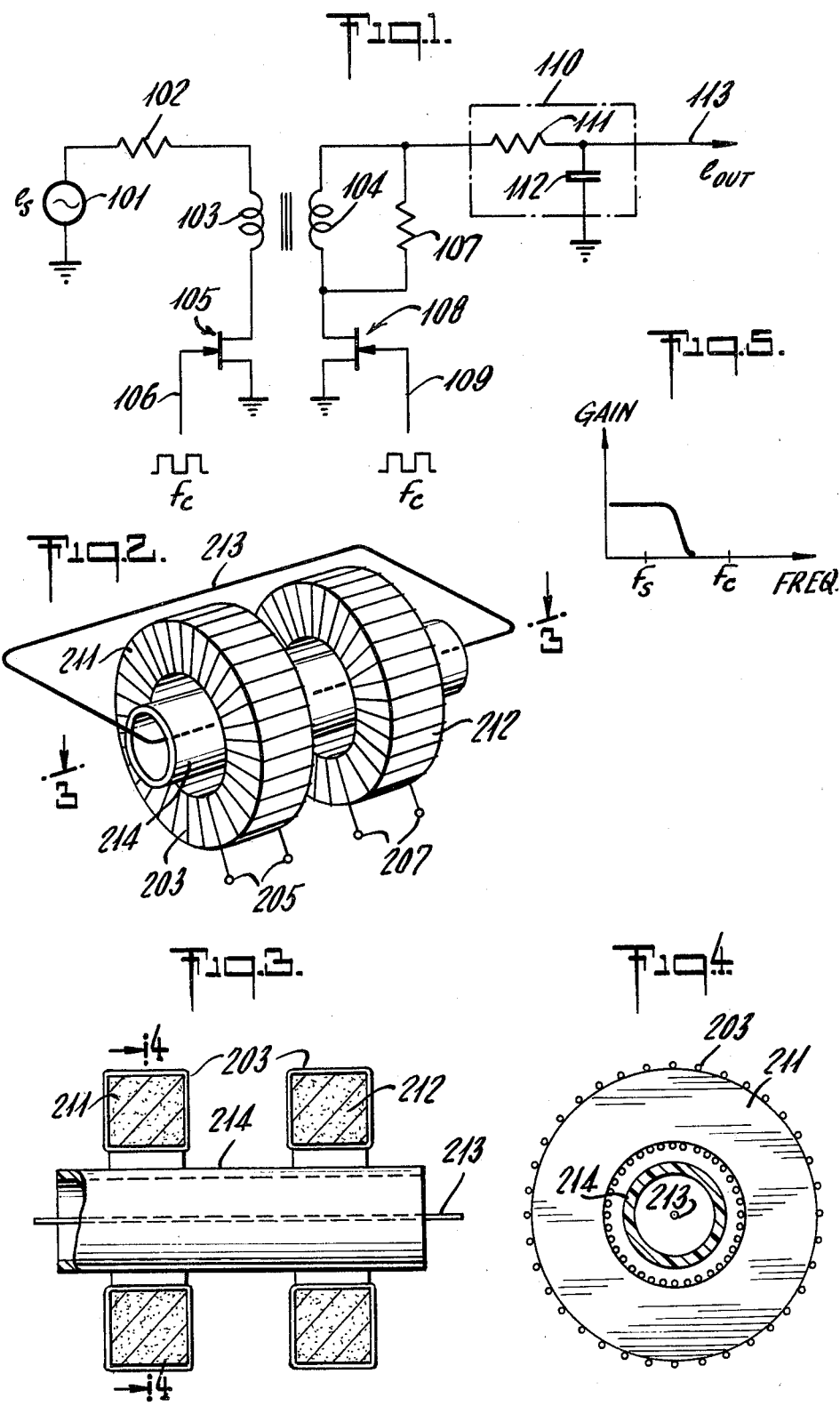

MAGNETICALLY COUPLED ISOLATION INTERFACE CIRCUIT

FIELD OF THE INVENTION

This invention relates to isolation/interface circuits, and more particularly to magnetically coupled circuits useful to isolate a patient from medical monitoring apparatus.

BACKGROUND OF THE INVENTION

The proliferation of extended capability medical monitoring instrumentation has tended, among other things, to increase the risk that a patient may be subjected to spurious or untoward electrical effects through the patient-monitoring device interface. Unless such possibilities are accounted for, there is a risk, at the minimum, that the data representing patient parameters being monitored will be subjected to interference, cross talk, or the like, and thus be rendered misleading as meaningless; at the maximum, that the patient actually is exposed to a risk of hazard. These risks are avoided by providing effective patient-utilization apparatus isolation units, whereby monitoring signals and the like from the patient are effectively and certainly delivered to the monitoring apparatus or the like utilization device, free of the abovementioned risks.

Numerous single channel and multiple signal isolated interference devices are commercially available, including those which use magnetic and optical coupling techniques.

Especially for patient monitoring applications, but no doubt generally in applications employing low signal levels but requiring a high degree of isolation security, optical coupling approaches are generally found wanting.

Typically, these approaches require too much isolated side power to operate the light sources, typically light emitting diodes; poor dynamic range or linearity; lack of ability readily to inspect isolation integrity; and all nevertheless require at least one transformer to pass power to the isolation side circuits.

Since a magnetic coupling will generally be required for purposes of conveyance of power, then, it is an object of the present invention to provide isolation interface circuits which utilize the magnetic coupling approach for patient to utilization apparatus signal channels as well, thereby obviating the need for any optical coupling, and the consequent drawbacks above specified.

It is a further object of the present invention to provide an approach to isolation interfacing wherein the magnetic coupling circuits are of moderate size, weight, and cost, are generally uniformly configured for power and for signal channel applications, and which provide isolation at quite high frequencies, perhaps in the range near 1 megahertz.

Yet another object of the present invention is to provide isolation interface circuits wherein the physical isolation is visually apparent to the user, thereby allowing the fact of the interface to be readily apparent to the user, and providing the physical, electrical, and psychological security inherent to such arrangements.

SUMMARY OF THE INVENTION

The present invention is premised on utilization of magnetic coupling, employing an appropriately designed transformer in an isolation circuit having a half balanced, suppressed carrier modulator/demodulator circuit functional in cooperation with the transformer. Judicious selection of modulator frequency, and demodulation filter characteristics, facilitates an extremely compact transformer design, preferably entailing respective primary and secondary toroidally wound annular ferrite cores, with a single coupling loop being maintained axially therewith by a tubular insulating member which also provides the actual visible physical and electrical isolation.

In a preferred embodiment, signals from a source, such as patient electroencephalograph signals, are coupled to one side of a primary winding, the other side of which is coupled to ground through the channel of a junction FET device. One side of the secondary winding is likewise coupled to ground through the channel of an FET device, and the other side of the secondary winding is coupled through a low pass filter to an output utilization device, such as the electroencephalograph signal processing apparatus. Both FET devices are synchronously operated (i.e., rendered conductive and nonconductive) at a relatively high frequency rate, thereby defining the carrier frequency for the modulating (i.e., primary) and the demodulating (i.e., secondary) sides of the isolation circuit. In a preferred embodiment, the modulating signals are provided from the power source on the secondary side, and coupled back to the primary, or patient side, by means of a transformer of similar design to the one bearing patient signals from the patient side to the monitoring side.

DESCRIPTION OF THE DRAWINGS

FIG. 1 shows in schematic form an isolation circuit embodying the principles of the present invention.

FIG. 2 shows a preferred transformer design for operation in the embodiment of FIG. 1.

FIGS. 3 and 4 show respective cross-sections of the embodiment of FIG. 2.

FIG. 5 shows an illustrative frequency bandwidth characteristic for the low pass filtering aspects of the circuit of FIG. 1.

BEST MODE FOR PRACTICING THE INVENTION

Referring first to FIG. 1., there is shown a preferred embodiment of the principles of the present invention. The signal source 101 is shown symbolically, and for present purposes it shall be assumed that the source is a patient being monitored, with the source voltage signal $e_s$ being particularly monitored patient functions, such as signals from an electroencephalograph channel. A resistor 102 symbolically represents the aggregate of resistance from the source, any resistance associated with the balance of the circuit, and as desired, any resistance which might be added by the designer such as to account for inductive or capacitive factors in the circuit, depending upon the frequency spectrum of the source voltage signal. From the resistor 102, the source signals $e_s$ are coupled to the primary winding 103 of a transformer 103–104, which primary is connected to ground or other suitable datum node through a switch 105. In a preferred embodiment, the switch 105 is a junction type field effect transistor, the channel of which interconnects the primary winding 103 with the datum. As shown, the FET 105 is alternatively opened and closed by a modulating or chopping signal at 106, having a modulating frequency designated $f_c$.

The secondary winding 104 of the transformer 103-104 is also coupled to ground or the like datum through a switch 108, which also preferably is a junction field effect transistor and which is operated by a signal at 109 which is synchronous with that at 106 and which employs the same chopping frequency $f_c$. A load resistor 107 is coupled in parallel with the secondary winding 104, and signals from the RL combination 104-107 are coupled through a low pass filter 110 to the output 113. In preferred form, the low pass filter 110 is embodied simply a capacitor 112 with resistor 111 (zero ohms for some applications).

The synchronous operation of switches 105 and 108 at a frequency $f_c$ is furnished to provide a relatively high frequency chopping rate, substantially larger than the frequency content, nominally designated $f_s$ of the signal $e_s$. Hence, the signal which is presented to the low pass filter 110 constitutes an intermittent or sampled signal at frequency $f_c$ having an envelope defined by patient monitoring signal $e_s$. The filter 110 integrates or smooths this signal, such that the output signal $e_s$ at 113 constitutes an amplitude scaled replica of the input signal $e_s$.

FIG. 5 shows an idealized transfer function for the filter 110, such that frequencies embodied in the principal signal $e_s$ are passed, whereas the chopping frequency $f_c$ and harmonics thereof are not.

A preferred form of a transformer 103-104 of the FIG. 1 circuit is shown isometrically in FIG. 2, and in various cross-sections in FIGS. 3 and 4. Considering FIGS. 2 through 4 together, the transformer 103-104 comprises a pair of conductive annular cores 211 and 212, which are respectively provided with toroidal windings 203 and 207 to constitute the primary and secondary windings of the transformer, respectively. The toroidally wound cores 211 and 212 are generally parallel to one another, and are penetrated by an insulating tubular member 214, which carries therein a wire 213, which in turn, as shown in FIG. 2, closes upon itself and constitutes a magnetic coupling between the primary and secondary toroidal windings 211 and 212. Hence, the insulating tubular member 214 provides spatial, physical, and electrical insulation between the conductors 203, 205, 207, and 213, and provides the magnetic coupling between primary winding 203 and secondary winding 207, via the toroidally wound cores 211 and 212.

In a preferred embodiment, wherein the signals to be conveyed through the isolation circuit have a two kilohertz bandwidth starting at 0 Hz (e.g., certain types of brain function monitors), a transformer may be fashioned wherein each toroid is in the range of four-tenths of an inch in diameter, the two vertically disposed toroids are spaced in the range of three-tenths of an inch apart, and the rigid rod support is in the range of one-eighths inch outer diameter and one-sixteenth inner diameter, and constituted of clear plastic material which is electrically non-conductive. In such an instance, the toroid primary and secondary coils are composed of ferrite cores of the type commercially available under the trade designation Ferroxcube No. 266T125 using 3E2A core material, and wound with number 30AWG enameled wire. The coupling link is advantageously composed of number 22AWG wire, and the respective windings are in the 25 to 50 turn range. For such a system, an advantageous composition for the low pass demodulator filter has a bandwidth from 0 Hz to approximately 3 kilohertz.

For such a preferred design, the one-half megahertz modulating signal provided to operate the junction FET devices is readily available, and may be coupled from the utilization device simultaneously to the secondary and primary of the FIG. 1 transformer by means of another transformer of identical design, but with the turns suitably selected to meet the power and speed requirements of the FET devices.

The foregoing has set forth preferred and illustrative embodiments of the principles of the present invention; it will be understood that numerous alternative embodiments will occur to those of ordinary skill in the art without departing from the spirit or the scope of the principles of the present invention.

I claim:

1. An isolation/interface circuit, for coupling signals having a given frequency bandwidth, from a source to a utilization apparatus comprising:
    (a) a transformer having primary and secondary windings, said source providing signals to said primary and said utilization apparatus receiving signals from said secondary;
    (b) first and second switch means, respectively serially connecting said primary and secondary windings to a datum;
    (c) means for synchronously alternately enabling and disabling said switch means at a predetermined frequency larger than any in said given frequency bandwidth;
    (d) low pass filter means serially intermediate said secondary winding and said utilization apparatus, said filter means having a frequency response characteristic which blocks signals at said predetermined frequency but which substantially passes said given frequency band.

2. A circuit as defined in claim 1 wherein said transformer includes:
    (a) first and second toroidally wound annular cores respectively defining said primary and secondary windings;
    (b) a generally tubular insulating member penetrating said cores; and
    (c) a closed conductive coupling link comprising at least one full turn which is carried by said insulating member through said cores, and which closes on itself outside of and out of contact with said cores.

3. A circuit as described in claim 2 wherein said first and second wound cores and said tubular member are substantially coaxially oriented with respect to one another, said coupling link being maintained substantially on the common axis.

4. A circuit as described in claim 1 wherein said first and second switch means are field effect transistor devices.

5. A transformer for utilization in a patient isolation interface circuit, patient signals being provided to a primary winding and utilization signals being taken from a secondary winding, magnetically coupled to the first winding, comprising:
    (a) first and second toroidally wound annular cores respectively defining said primary and secondary windings;
    (b) a generally tubular insulating member penetrating said cores; and
    (c) a closed conductive coupling link comprising at least one full turn which is carried by said insulating member through said cores, and which closes on itself outside of and out of physical and electrical contact with said cores.

6. A transformer as described in claim 5 wherein said first and second wound cores and said tubular member are substantially coaxially oriented, said coupling link being maintained substantially on the common axis.

* * * * *